US012582437B2

(12) United States Patent
Urbanski et al.

(10) Patent No.: US 12,582,437 B2
(45) Date of Patent: Mar. 24, 2026

(54) NEEDLE AND ASSEMBLY OF NEEDLE, GUIDEWIRE, AND/OR CATHETER INSERT

(71) Applicant: Boston Scientific Medical Device Limited, Galway (IE)

(72) Inventors: John Paul Urbanski, Toronto (CA); Berna Erdemir, North York (CA); Ferryl Alley, Burlington (CA)

(73) Assignee: Boston Scientific Medical Device Limited, Galway (IE)

( * ) Notice: Subject to any disclaimer, the term of this patent is extended or adjusted under 35 U.S.C. 154(b) by 504 days.

(21) Appl. No.: 18/160,661

(22) Filed: Jan. 27, 2023

(65) Prior Publication Data
US 2024/0041493 A1 Feb. 8, 2024

Related U.S. Application Data

(63) Continuation of application No. PCT/IB2021/056516, filed on Jul. 19, 2021.

(60) Provisional application No. 63/056,851, filed on Jul. 27, 2020.

(51) Int. Cl.
*A61B 17/34* (2006.01)
*A61M 25/09* (2006.01)

(52) U.S. Cl.
CPC ...... *A61B 17/3415* (2013.01); *A61B 17/3417* (2013.01); *A61M 25/09* (2013.01)

(58) Field of Classification Search
CPC ............ A61B 17/3415; A61B 17/3417; A61B 17/3478; A61B 2017/22038; A61B 2090/0801; A61M 25/09

USPC .......................................................... 606/185
See application file for complete search history.

(56) References Cited

U.S. PATENT DOCUMENTS

| | | | |
|---|---|---|---|
| 9,533,120 B1 * | 1/2017 | Kimmel ................ | A61M 25/06 |
| 2002/0087076 A1 | 7/2002 | Meguro et al. | |
| 2005/0149062 A1 * | 7/2005 | Carroll ............... | A61B 17/3478 |
| | | | 606/129 |
| 2006/0064062 A1 * | 3/2006 | Gurusamy .......... | A61M 25/065 |
| | | | 604/164.01 |
| 2008/0045908 A1 * | 2/2008 | Gould ................... | A61M 25/09 |
| | | | 604/272 |

(Continued)

OTHER PUBLICATIONS

International Search Report for PCT Application No. PCT/IB2021/056516 mailed Oct. 21, 2021.

(Continued)

*Primary Examiner* — Jocelin C Tanner
(74) *Attorney, Agent, or Firm* — Nelson Mullins Riley & Scarborough LLP

(57) ABSTRACT
A needle includes a hub and an elongate body. The elongate body has a proximal portion joined to the hub and defining a proximal end, a distal portion opposite the proximal portion and defining a distal end, and an intermediate portion between the proximal portion and the distal portion and having a first end adjacent the proximal portion and a second end adjacent the distal portion. A lumen extends longitudinally through the elongate body. The proximal portion extends linearly along a longitudinal axis and has a proximal diameter. The distal portion is curved to space the distal end away from the longitudinal axis and has a distal diameter that is less than the proximal diameter. The intermediate portion tapers in outer diameter going from the first end to the second end.

20 Claims, 8 Drawing Sheets

(56)                References Cited

U.S. PATENT DOCUMENTS

2009/0275862 A1*  11/2009  Elsesser ................ A61M 25/09
                                                            600/585
2014/0180164 A1     6/2014  Mcghie
2018/0036060 A1*    2/2018  Wegrzyn, III  ....... A61B 18/082
2021/0162181 A1*    6/2021  Endo .................. A61B 17/3478

OTHER PUBLICATIONS

Kumar S, et al., "Needle in needle epicardial access: Preliminary oberservations with a modified technique for facilitating epicardial interventional procedures," Heart Rythm, vol. 12, No. 7, pp. 1691-1697, Jul. 2015.

* cited by examiner

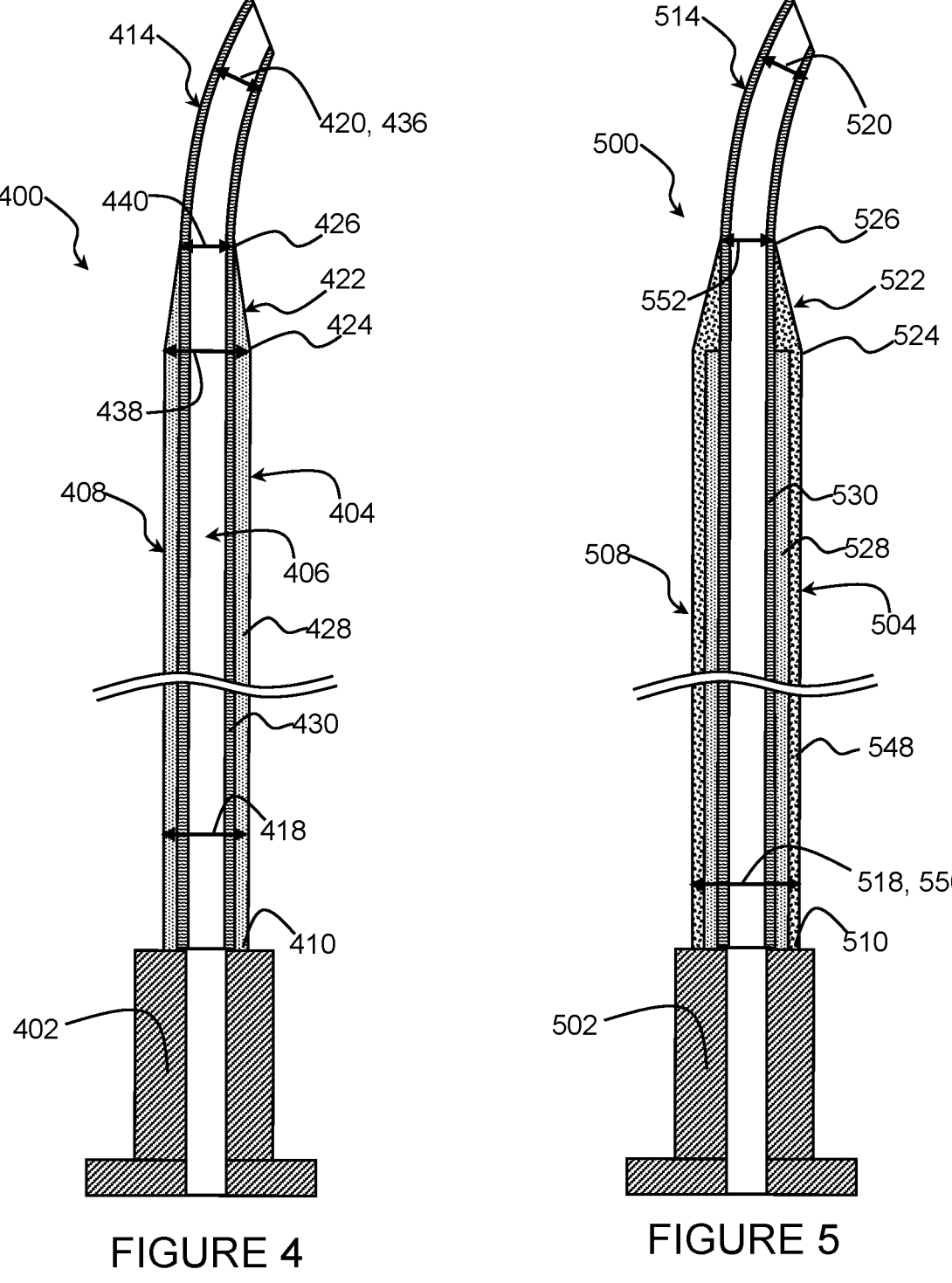
FIGURE 4                    FIGURE 5

NEEDLE AND ASSEMBLY OF NEEDLE, GUIDEWIRE, AND/OR CATHETER INSERT

CROSS REFERENCE TO RELATED APPLICATION

This application is a continuation application of International Application No. PCT/162021/056516, filed Jul. 19, 2021, titled "NEEDLE AND ASSEMBLY OF NEEDLE, GUIDEWIRE, AND/OR CATHETER INSERT," which claims priority to U.S. Provisional Application No. 63/056, 851, filed Jul. 27, 2020, titled "NEEDLE AND ASSEMBLY OF NEEDLE, GUIDEWIRE, AND/OR CATHETER INSERT," the entire disclosures of which are incorporated herein by reference.

FIELD

This document relates to needles, such as those used in medical procedures. More specifically, this document relates to needles and to assemblies including needles, guidewires, and/or catheter inserts.

SUMMARY

The following summary is intended to introduce the reader to various aspects of the detailed description, but not to define or delimit any invention.

Needles are disclosed. According to some aspects, a needle includes a hub and an elongate body. The elongate body has a proximal portion joined to the hub and defining a proximal end of the elongate body, a distal portion opposite the proximal portion and defining a distal end of the elongate body, and an intermediate portion between the proximal portion and the distal portion and having a first end adjacent the proximal portion and a second end adjacent the distal portion. A lumen extends longitudinally through the elongate body. The proximal portion extends linearly along a longitudinal axis and has a proximal diameter. The distal portion is curved to space the distal end away from the longitudinal axis and has a distal diameter that is less than the proximal diameter. The intermediate portion tapers in outer diameter going from the first end to the second end.

In some examples, the elongate body includes an outer shaft and an inner shaft received in the outer shaft and defining the lumen.

In some examples, the outer shaft extends between the proximal end and the first end of the intermediate portion and has an outer shaft diameter that is constant. The inner shaft can extend between the proximal end and the distal end and can have an inner shaft diameter that is constant. The outer shaft diameter can define the proximal diameter and the inner shaft diameter can define the distal diameter.

In some examples, a filler is received on the inner shaft in the intermediate portion. The filler can taper in diameter going from the first end to the second end. The filler can have a first diameter at the first end and a second diameter at the second end. The first diameter can be equal to the proximal diameter, and the second diameter can be equal to the distal diameter.

In some examples, the elongate body further includes a sleeve in which the inner shaft and outer shaft are received. The sleeve can extend between the proximal end and the second end of the intermediate portion. The sleeve can have a first sleeve diameter that is constant between the proximal end and the first end of the intermediate portion. The sleeve can taper in diameter between the first end and the second end of the intermediate portion. The first sleeve diameter can define the proximal diameter. The sleeve can have a second diameter at the second end. The second diameter can be equal to the distal diameter.

In some examples, the outer shaft extends between the proximal end and the second end of the intermediate portion. The outer shaft can have an outer shaft diameter that is constant between the proximal end and the first end of the intermediate portion. The outer shaft diameter can define the proximal diameter. The outer shaft can taper in diameter between the first end and the second end. The outer shaft can have a first diameter at the first end and a second diameter at the second end. The first diameter can be equal to the proximal diameter and the second diameter can be equal to the distal diameter.

In some examples, the elongate body is of a one-piece construction.

In some examples, the hub includes an indicator of a direction of the curve of the distal portion.

In some examples, the elongate body includes an inner surface defining the lumen and an outer surface spaced radially from the inner surface. At the distal end, the inner surface can be radiused.

In some examples, the proximal diameter is at most about 17 gauge, and the distal diameter is at least about 19 gauge.

Medical assemblies are also disclosed.

According to some aspects, a medical assembly includes a needle and a guidewire. The needle includes a hub, an elongate body, and a lumen. The elongate body has a proximal portion joined to the hub and defining a proximal end, a distal portion opposite the proximal portion and defining a distal end, and an intermediate portion between the proximal portion and the distal portion and having a first end adjacent the proximal portion and a second end adjacent the distal portion. The lumen extends longitudinally through the elongate body. The proximal portion extends linearly along a longitudinal axis and has a proximal diameter. The distal portion is curved to space the distal end away from the longitudinal axis and has a distal diameter that is less than the proximal diameter. The intermediate portion tapers in diameter going from the first end to the second end. The guidewire is advanceable through the lumen from the proximal end to the distal end.

In some examples, the guidewire has a guidewire distal portion and a guidewire proximal portion. The guidewire can include a core wire and a coil received on the core wire in the distal portion. The guidewire can have a smooth transition between the core wire and the coil.

In some examples, to provide the smooth transition, the core wire includes a ramp proximal of the coil.

In some examples, to provide the smooth transition, the core wire includes a cut-out in which the coil is seated.

In some examples, the assembly further includes a catheter insert that is received in the lumen and that has a shield. The catheter insert can be movable between a retracted configuration in which the shield is received in the lumen, and a deployed configuration in which the shield is positioned proud of the distal end of the needle and shields the guidewire from the distal end of the needle during retracting of the guidewire.

According to some aspects, a medical assembly includes a needle, a guidewire, and a catheter insert. The needle includes a hub, an elongate body, and a lumen extending longitudinally through the elongate body. The elongate body has a proximal portion joined to the hub and defining a proximal end of the elongate body, and a distal portion opposite the proximal portion and defining a sharp distal end of the elongate body. The guidewire is advanceable through the lumen to position a guidewire distal portion proud of the sharp distal end, and is retractable through the lumen to withdraw the guidewire distal portion back into the lumen; The catheter insert is received in the lumen and has a shield. The catheter insert is movable between a retracted configuration in which the shield is received in the lumen and a deployed configuration in which the shield is positioned proud of the sharp distal end and shields the guidewire from the sharp distal end during retracting of the guidewire. In some examples, the catheter insert includes a sleeve and the shield includes a tip of the sleeve.

In some examples, the shield includes a shoulder surface that covers the sharp distal end when the shield is in the deployed configuration.

In some examples, the shield is resiliently flexible and automatically snaps radially outwardly when the shield is advanced proud of the distal end.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIG. 4 is a cross-section similar to that of FIG. 2, taken through another example needle;

FIG. 5 is a cross-section similar to that of FIG. 2, taken through another example needle;

DETAILED DESCRIPTION

Various apparatuses or processes or compositions will be described below to provide an example of an embodiment of the claimed subject matter. No embodiment described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are needles and assemblies of needles, guidewires, and/or catheter inserts. The needles can be used, for example, to access the pericardial space (e.g. for diagnosis and treatment of arrhythmias). The needles can be configured to have a relatively small diameter distal portion (e.g. about 19 gauge or 20 gauge), which can facilitate patient safety (e.g. by preventing or minimizing tissue damage and/or scarring), while having a relatively high column strength, which can facilitate pushability of the needle. Furthermore, the guidewires can be configured to have a relatively smooth transition between the core wire and the coil thereof, which can prevent or reduce the risk of snagging of the guidewire on the distal end of the needle. Furthermore, the catheter inserts can be configured to selectively obstruct a sharp distal end of the needles, to prevent snagging of the guidewire on the sharp distal end of the needle during retraction of the guidewire.

Figure 1:
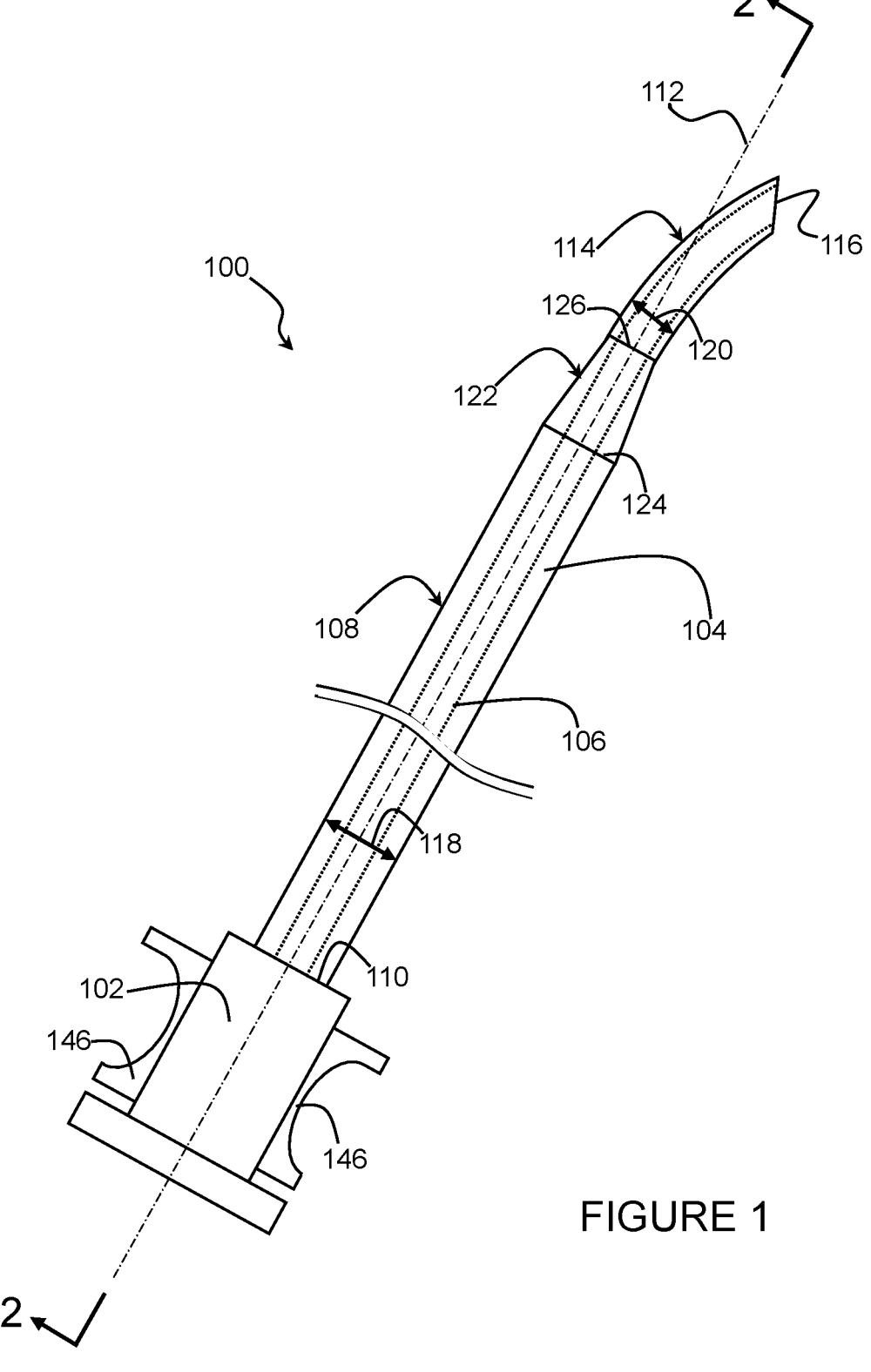
FIG. 1 is a side view of an example needle.

Referring now to FIG. 1, a first example of a needle 100 is shown. The needle 100 generally includes a hub 102, which can be used to hold and maneuver the needle 100. The hub 102 can optionally be configured as a luer lock, to allow a syringe or other device to be attached thereto. The needle 100 further includes elongate body 104 extending from the hub 102, which can be used for puncturing tissue, and a lumen 106 (shown in dotted line) extending longitudinally through the elongate body 104, through which additional devices (e.g. a stylet, a catheter insert as described below, and/or a guidewire as described below) can be advanced or through which a fluid can be delivered.

Referring still to FIG. 1, the elongate body 104 includes a proximal portion 108 that is joined to the hub 102. The proximal portion 108 defines a proximal end 110 of the elongate body 104. The proximal portion 108 is generally elongate and extends linearly along a longitudinal axis 112 of the elongate body 104.

Referring still to FIG. 1, the elongate body 104 further includes a distal portion 114 that is opposite the proximal portion 108. The distal portion 114 defines a distal end 116 of the elongate body 104. The distal portion 114 is curved to space the distal end 116 away from the longitudinal axis 112. The curve can allow for the user to direct the distal end 116 in a desired direction (e.g. away from heart muscle) and can prevent coring.

Referring still to FIG. 1, the proximal portion 108 has an outer diameter 118 (also referred to herein as a 'proximal diameter') that is relatively large (e.g. at most about 17 gauge, or about 17 gauge), and the distal portion 114 has an outer diameter 120 (also referred to herein as a 'distal diameter') that is relatively small—i.e. less than the proximal diameter 118 (e.g. the distal diameter can be at least about 19 gauge, or about 19 gauge, or about 20 gauge). Providing the distal portion 114 with a relatively small outer diameter can facilitate patient safety, while providing the proximal portion 108 with a relatively large outer diameter can facilitate pushability of the needle 100.

Referring still to FIG. 1, the elongate body further includes an intermediate portion 122 between the proximal portion 108 and the distal portion 114. The intermediate portion 122 extends between a first end 124, which is adjacent the proximal portion 108, and a second end 126, which is adjacent the distal portion 114. The intermediate portion 122 tapers in outer diameter going from the first end 124 to the second end 126, to provide a smooth transition between the proximal portion 108 and the distal portion 114.

Figure 2:
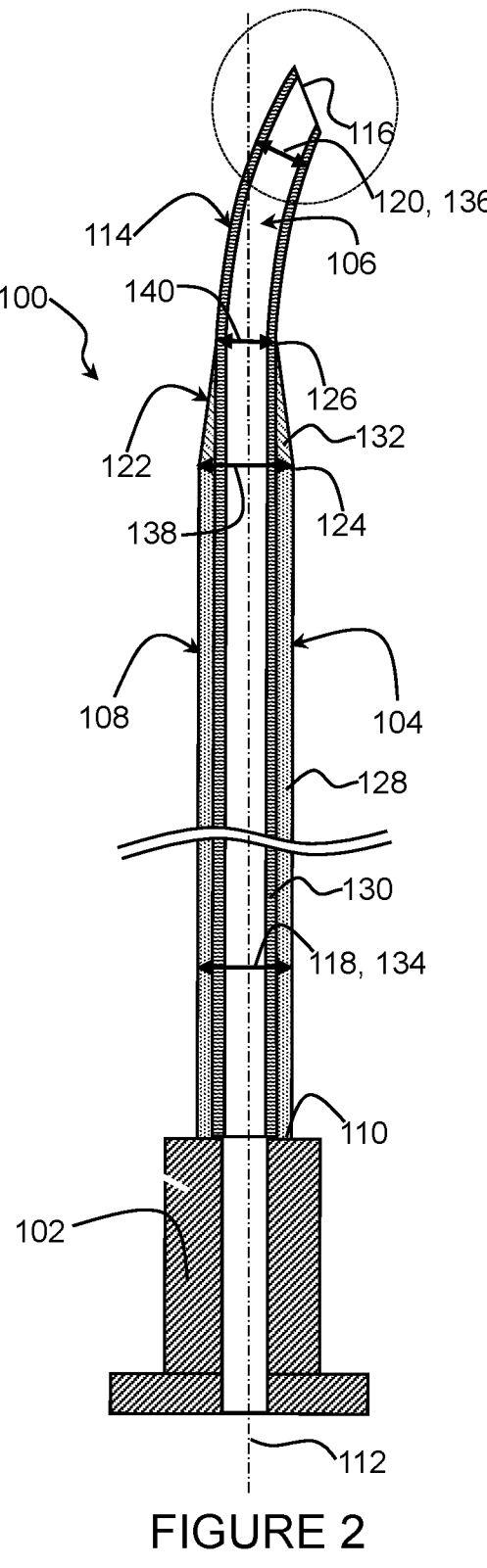
FIG. 2 is a cross-section taken along line 2-2 in FIG. 1.

Referring now to FIG. 2, in the example shown, the elongate body 104 is of a three-piece construction, and includes an outer shaft 128, an inner shaft 130, and a filler 132. The outer shaft 128 extends between the proximal end 110 and the first end 124 of the intermediate portion 122. The outer shaft 128 has an outer diameter 134 (also referred to herein as an 'outer shaft diameter') that is generally constant and that defines the proximal diameter 118. The inner shaft 130 is received in the outer shaft 128 and defines the lumen 106. The inner shaft 130 extends between the proximal end 110 and the distal end 116 and extends proud of the outer shaft 128. The inner shaft 130 has an outer diameter 136 (also referred to herein as an 'inner shaft diameter') that is generally constant and that defines the distal diameter 120. The filler 132 is received on the inner shaft 130 in the intermediate portion 122, distally of and adjacent the outer shaft 128. The filler tapers 132 in outer diameter going from the first end 124 to the second end 126 thereof, to provide the smooth transition between the proximal portion 108 and the distal portion 114. That is, the filler has a first diameter 138 at the first end 124 and a second diameter 140 at the second end. The first diameter 138 is equal to the proximal diameter 118, and the second diameter 140 is equal to the distal diameter 120.

Referring still to FIG. 2, the inner shaft 130 and outer shaft 128 can both be, for example, metal (e.g. stainless steel) tubes that are welded or soldered or adhered together. The filler 132 can be, for example, a solder material.

Figure 3:
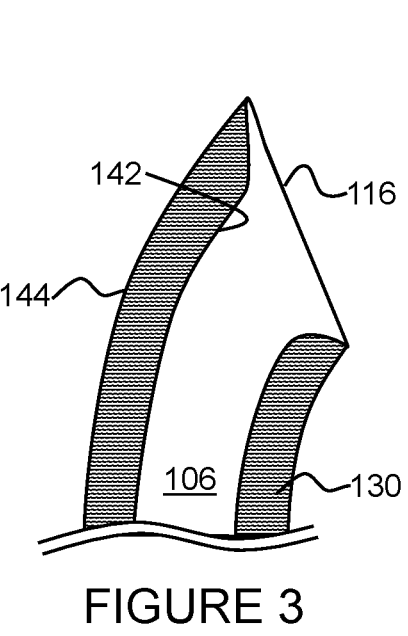
FIG. 3 is an enlarged view the encircled region of FIG. 2.

Referring now to FIG. 3, in the example shown, the distal end 116 is sharp. That is, in example shown, the distal end is beveled, to provide sharpness and facilitate puncture of tissue. However, in order to prevent a guidewire (not shown in FIG. 3) from snagging on the distal end 116, the "heel" of the bevel is radiused. More specifically, inner shaft 130 has an inner surface 142 that defines the lumen 106, and an outer surface 144 that is spaced radially from the inner surface 142. At the distal end 116, the inner surface 142 is radiused.

Referring back to FIG. 1, in the example shown, the hub 102 includes an indicator for indicating the direction of the curve of the distal portion 114 (i.e. to indicate to the user the direction in which the curved distal portion 114 is oriented, if the curved distal portion 114 itself is not visible). In the example shown, the indicator includes a pair of wings 146, that are aligned with the curve of the distal portion 114.

Referring now to FIG. 4, an alternative example of a needle is shown. In FIG. 4, features that are similar to those of FIGS. 1 to 3 are labelled with similar reference numerals, incremented by 300. Similarly to the needle 100, the needle 400 includes a hub 402 and an elongate body 404, which includes a curved distal portion 414 having a relatively small distal diameter 420, a linear proximal portion 408 having a relatively large proximal diameter 418, and an intermediate portion 422 that tapers in diameter going from the proximal portion 408 to the distal portion 414.

Referring still to FIG. 4, in the example shown, the elongate body 404 is of a two-piece construction, and includes an inner shaft 430 and an outer shaft 420. The outer shaft 428 extends between the proximal end 410 of the elongate body 404 and the second end 426 of the intermediate portion 422. The outer shaft 428 provides the taper in the intermediate portion 422. That is, the outer shaft 428 has an outer diameter that is constant between the proximal end 410 of the elongate body 404 and the first end 424 of the intermediate portion. The outer shaft 428 then tapers in outer diameter between the first end 424 of the intermediate portion 422 and the second end 426 of the intermediate portion 422. Particularly, the outer shaft 428 has a first diameter 438 at the first end 424 of the intermediate portion 422, and a second diameter 440 at the second end 426 of the intermediate portion 422. The first diameter 438 is equal to the proximal diameter 418 and the second diameter 440 is equal to the distal diameter 420. The inner shaft 430 is received in the outer shaft 428 and defines the lumen 406. The inner shaft 430 extends between the proximal end 410 and the distal end 416 of the elongate body 404 and extends proud of the outer shaft 428. The inner shaft 430 has an outer diameter 436 that is generally constant and that defines the distal diameter 420.

Referring now to FIG. 5, an alternative example of a needle is shown. In FIG. 5, features that are similar to those of FIGS. 1 to 3 are labelled with similar reference numerals, incremented by 400. Similarly to the needle 100, the needle 500 includes a hub 502 and an elongate body 504, which includes a curved distal portion 514 having a relatively small distal diameter 520, a linear proximal portion 508 having a relatively large proximal diameter 518, and an intermediate portion 522 that tapers in diameter going from the proximal portion 508 to the distal portion 514.

Referring still to FIG. 5, the elongate body 504 includes an inner shaft 530 and an outer shaft 528, which are generally of the same configuration as the inner shaft 130 and outer shaft 128 of FIGS. 1 to 3. However, rather than a filler, the elongate body 504 includes a sleeve 548 (e.g. a polymer sleeve) in which the inner shaft 530 and the outer shaft 528 are received. The sleeve 548 extends between the proximal end 510 of the elongate body 504 and the second end 526 of the intermediate portion 522. The sleeve 548 has an outer diameter 550 (also referred to herein as a 'first sleeve diameter') that is constant between the proximal end 510 and the first end 524 of the intermediate portion 522. The sleeve 548 than tapers in outer diameter between the first end 524 and second end 526 of the intermediate portion (to a 'second sleeve diameter' 552). The first sleeve diameter 550 defines the proximal diameter 510, and the second sleeve diameter 552 is equal to the distal diameter 520.

Figure 6:
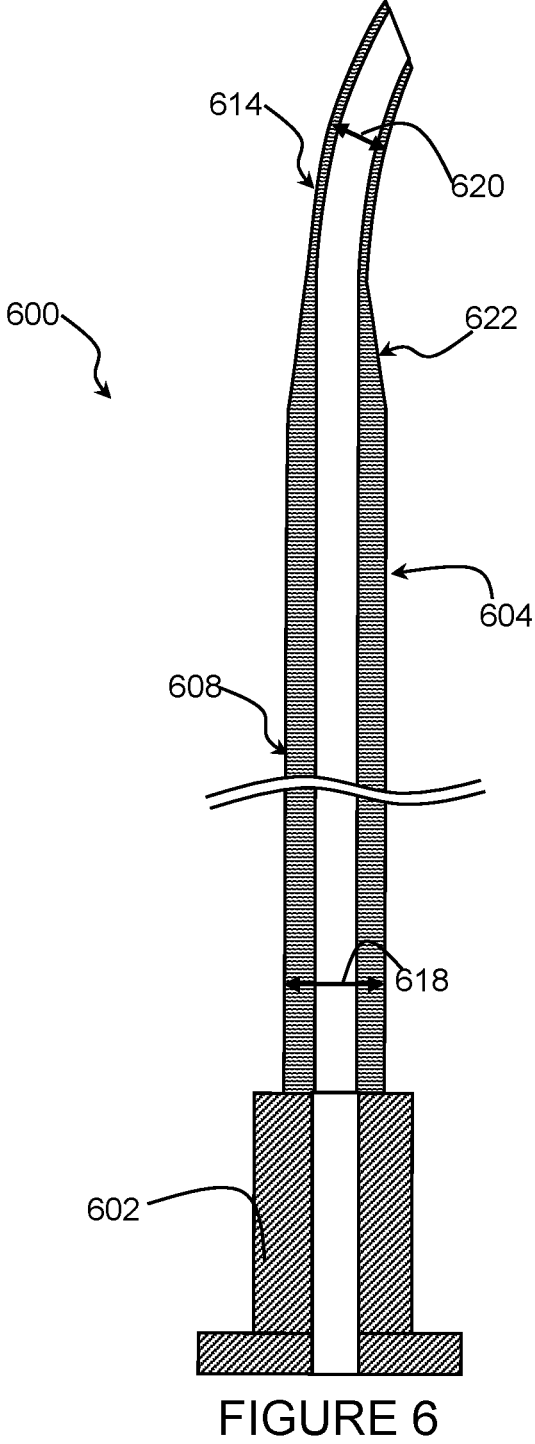
FIG. 6 is a cross-section similar to that of FIG. 2, taken through another example needle.

Referring now to FIG. 6, an alternative example of a needle is shown. In FIG. 6, features that are similar to those of FIGS. 1 to 3 are labelled with similar reference numerals, incremented by 500. Similarly to the needle 100, the needle 600 includes a hub 602 and an elongate body 604, which includes a curved distal portion 614 having a relatively small distal diameter 620, a linear proximal portion 608 having a relatively large proximal diameter 618, and an intermediate portion 622 that tapers in diameter going from the proximal portion 608 to the distal portion 614. However, in the example of FIG. 6, the elongate body 604 is of a one-piece construction. For example, the elongate body 604 can be a custom extruded metallic (e.g. stainless steel) tube.

Various guidewires may be used with the needles described herein. In some examples, such guidewires may have a guidewire proximal portion and a guidewire distal portion, and may include a core wire and a coil (e.g. a radiopaque coil) on the core wire in the guidewire distal portion. Such guidewires may be used by advancing the guidewire through the lumen of the elongate body, from the proximal end to the distal end of the elongate body, to position the guidewire distal portion proud of the distal end of the elongate body. After use, the guidewire may be retracted to withdraw the guidewire distal portion back into the lumen. In order to prevent snagging of the guidewire distal portion (e.g. snagging of the coil) on the relatively small distal end of the elongate body during retraction of the guidewire, guidewires intended for use with the needles disclosed herein may be configured to have a smooth transition between the core wire and the coil.

Figures 7, 8, 9:
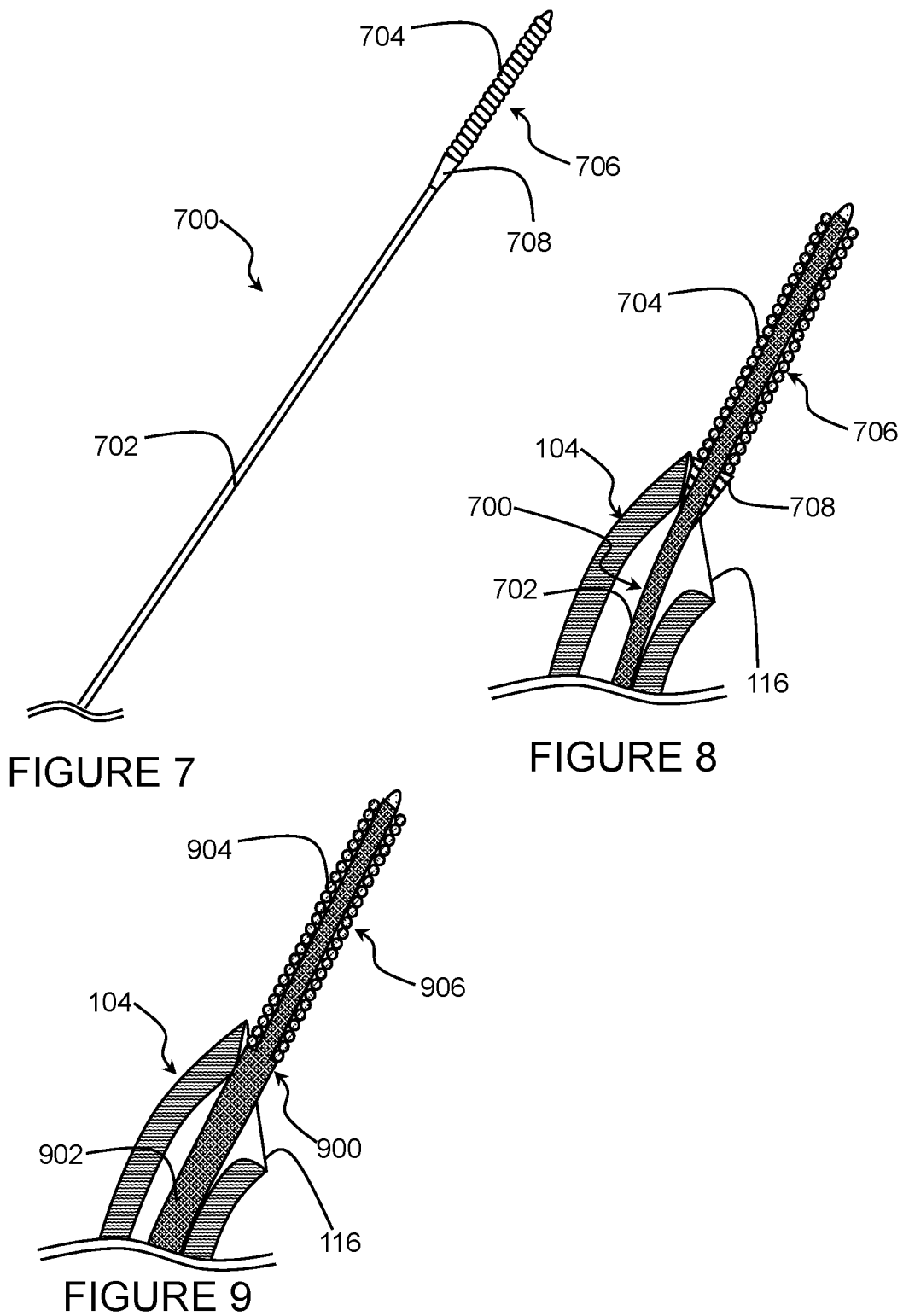
FIG. 7 is a partial perspective view of an example guidewire.
FIG. 8 is a partial cross-section showing the guidewire of FIG. 7 received in the needle of FIG. 1.
FIG. 9 is a partial cross-section similar to that of FIG. 8, showing another example guidewire.

For example, referring to FIG. 7, an example guidewire 700 is shown that includes a core wire 702 and a coil 704 on the core wire 702 in the guidewire distal portion 706. The guidewire 700 further includes a ramp 708 proximal of the coil 704, to smooth the transition between the coil 704 and the core wire 702, and prevent snagging on the distal end 116 of the elongate body 104 of the needle 100 (shown in FIG. 8) during retraction of the guidewire.

For further example, referring to FIG. 9, another example guidewire 900 is shown that includes a core wire 902 and a coil 904 on the core wire 902 in the guidewire distal portion 906. In order to provide a smooth transition, the guidewire 900 includes a cut-out in the guidewire distal portion 906, and the coil 904 is seated in the cut-out.

Figures 10, 11:
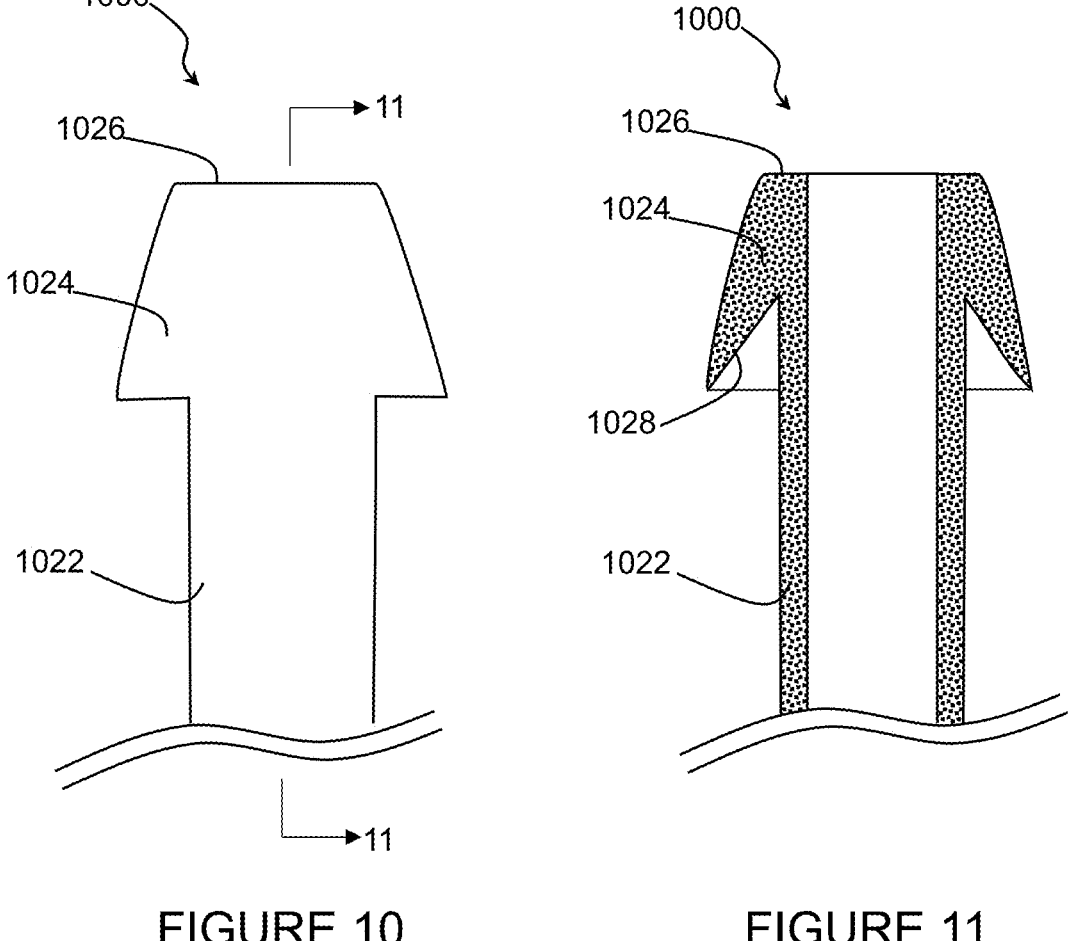
FIG. 10 is a partial side view of an example catheter insert.
FIG. 11 is a cross-section taken along line 11-11 in FIG. 10.
Figures 12, 13:
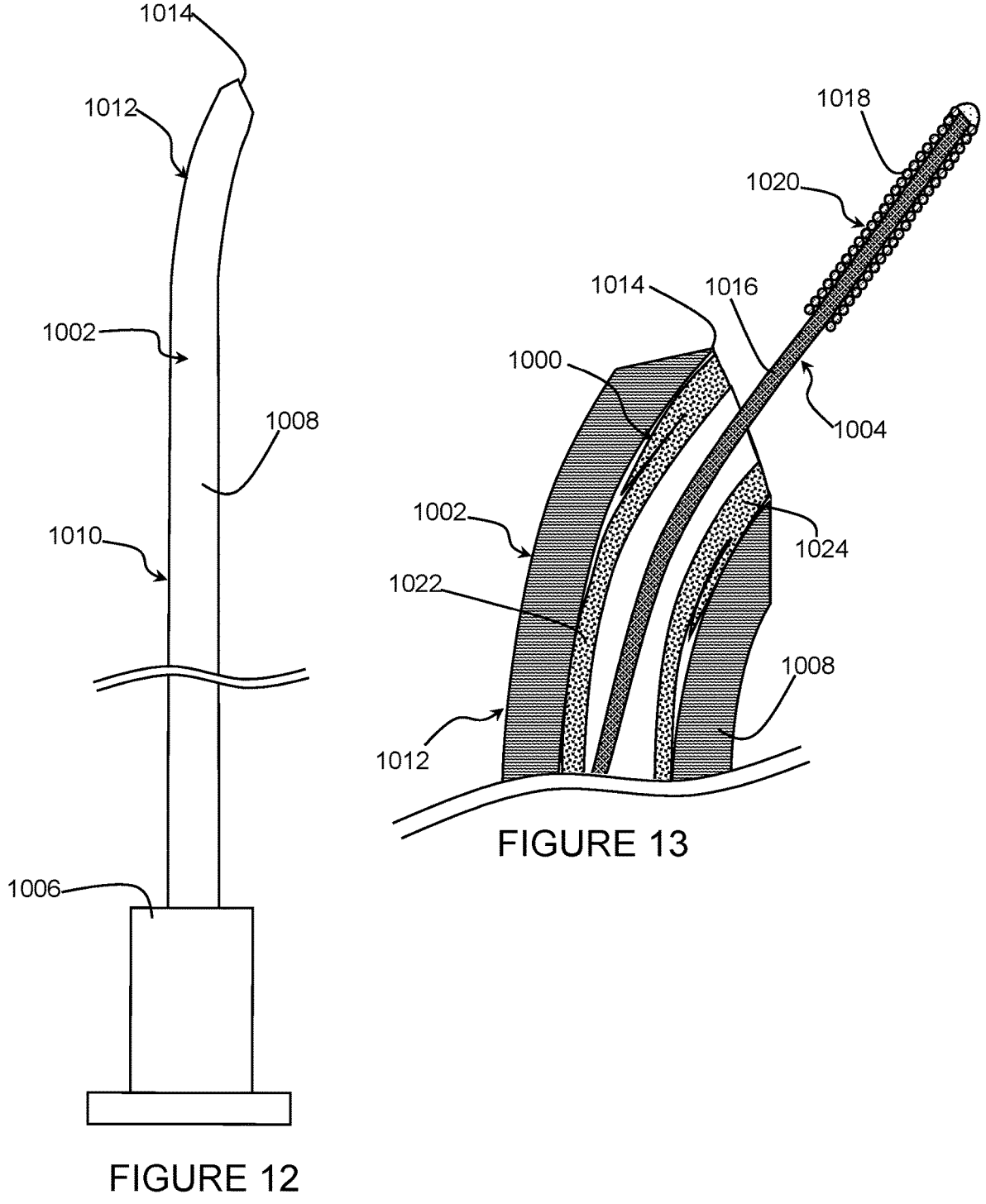
FIG. 12 is a side view of an assembly including the catheter insert of FIGS. 10 and 11, a needle, and a guidewire, where the catheter insert is in a retracted configuration.
FIG. 13 is an enlarged cross-sectional view of a portion of the assembly of FIG. 12.

Referring now to FIGS. 10 and 11, a catheter insert 1000 is shown. An assembly of the catheter insert 1000, a needle 1002, and a guidewire 1004 is shown in FIGS. 12 to 15. As will be described in more detail below, the catheter insert 1000 serves to shield the guidewire 1004 from a sharp distal end of the needle 1002 during retraction of the guidewire 1004, in order to prevent snagging of the guidewire 1004 (e.g. snagging of a guidewire distal portion, such as a coil of the guidewire) on the sharp distal end of the needle 1002 during retraction of the guidewire 1004. In FIGS. 12 and 13, the catheter insert 1000 is shown in a retracted configuration, and in FIGS. 14 and 15, the catheter insert 1000 is shown in a deployed configuration.

Assemblies such as that shown in FIGS. 12 to 15 can include various needles, including any of the needles described above; however, in the example shown, the needle 1002 is of a simplified configuration. That is, the needle includes a hub 1006 and an elongate body 1008, and the elongate body 1008 is of a one-piece construction that has a generally constant diameter. The elongate body 1008 includes a linear proximal portion 1010 and a curved distal portion 1012. The distal portion 1012 defines a distal end 1014 that is sharp. A lumen (not labelled) extends through the elongate body. Furthermore, assemblies such as that shown in FIGS. 12 to 15 can include various guidewires, such any of the guidewires described above; however, in the example shown, the guidewire 1004 is of a simplified configuration, and includes a core wire 1016, and a coil 1018 on the core wire 1016 in the guidewire distal portion 1020.

Referring back to FIGS. 10 and 11, in the example shown, the catheter insert 1000 is in the form of a sleeve 1022. A tip of the sleeve forms a shield 1024 that in use, shields the guidewire 1004 from the sharp distal end 1014 of the needle 1002 during retracting of the guidewire 1004. The shield 1024 has a generally blunt end surface 1026, and a proximally facing surface that defines a shoulder 1028 for engaging and covering the sharp distal end 1014 of the elongate body 1008 in use. The shield 1024 is resiliently flexible, so that it can collapse to be received within the lumen of the elongate body 1008, and can pop or snap outwardly (to the configuration shown in FIGS. 10 and 11) when it exits the elongate body 1008. Furthermore, the shield 1024 can be generally strong, to prevent damage to the shield 1024 from the sharp distal end 1014 of the elongate body 1008. For example, the sleeve 1022, including the shield 1024, can be fabricated from a plastic such as high density polyethylene (HDPE).

Figures 14, 15:
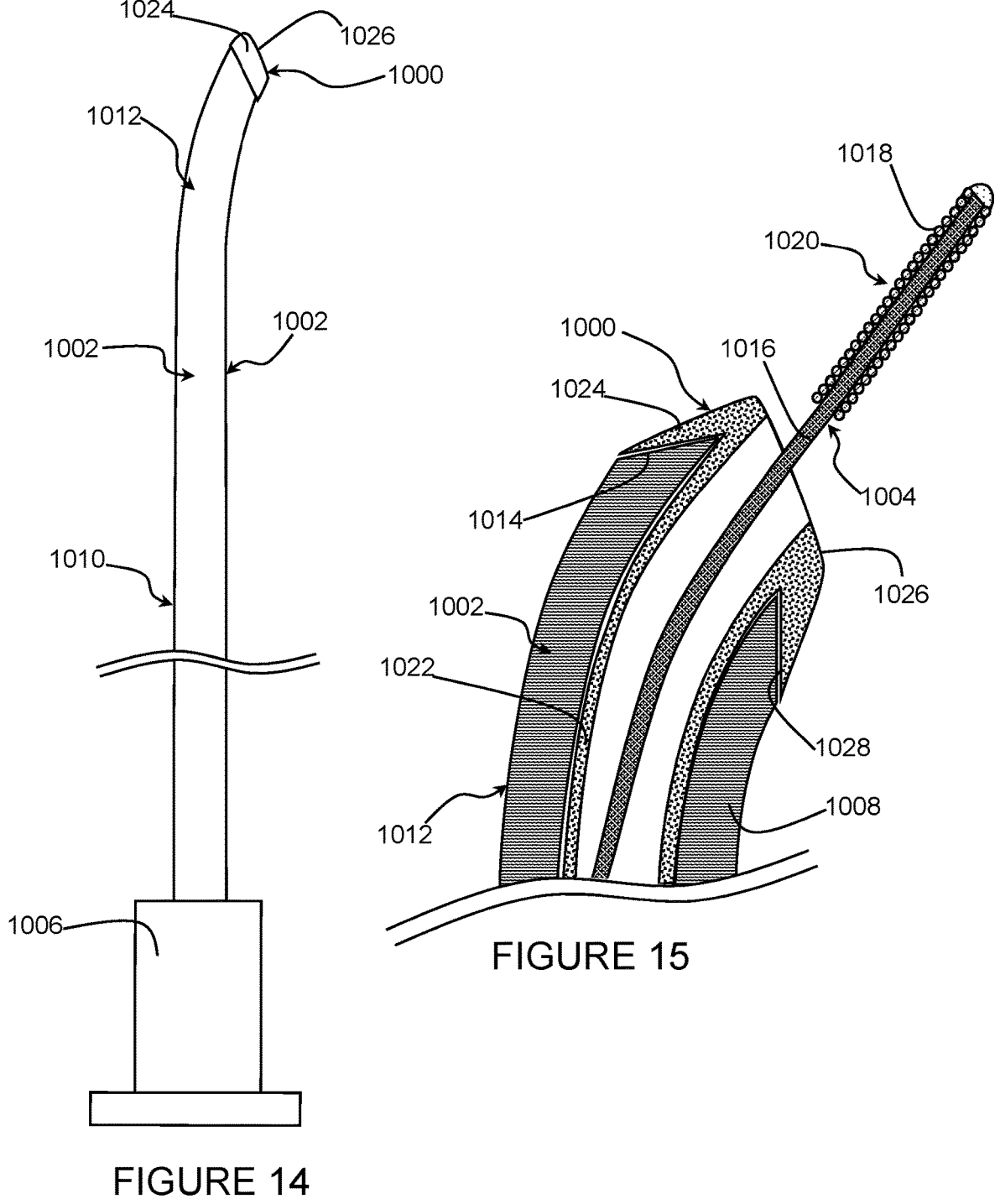
FIG. 14 is a side view of the assembly of FIGS. 12 and 13, where the catheter insert is in a deployed configuration.
FIG. 15 is an enlarged cross-sectional view of a portion of the assembly of FIG. 14.

Referring now to FIGS. 12 and 13, the catheter insert 1000 is shown in a retracted configuration, in which the sleeve 1022, including the shield 1024, is received in the lumen of the elongate body 1008. During advancement and use of the guidewire 1004, the catheter insert 1000 can remain in the retracted configuration, with the guidewire 1004 passing therethrough. Referring next to FIGS. 14 and 15, prior to retracting the guidewire 1004, the catheter insert 1000 can be moved to the deployed configuration. This can be achieved by advancing the catheter insert 1000 so that the shield 1024 is positioned proud of the sharp distal end 1014 of the elongate body 1008. When the shield 1024 exits the elongate body 1008, it will pop or snap radially outwardly, due to its resiliently flexible nature. The catheter insert 1000 can then be withdrawn slightly, so that the shoulder 1028 of the shield 1024 abuts and covers the sharp distal end 1014 of the elongate body 1008, and the blunt end surface 1026 of the shield 1024 faces towards the guidewire distal portion 1020. When the guidewire 1004 is then withdrawn, it will be protected from the sharp distal end 1014 of the elongate body 1008 by the shield 1024, and the risk of damage to the guidewire 1004 will be mitigated. While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A needle for puncturing tissue, the needle comprising:

a hub;

an elongate body having a proximal portion joined to the hub and defining a proximal end of the elongate body, a distal portion opposite the proximal portion and defining a distal end of the elongate body, and an intermediate portion between the proximal portion and the distal portion and having a first end adjacent the proximal portion and a second end adjacent the distal portion; and a lumen extending longitudinally through the elongate body;

wherein the proximal portion extends linearly along a longitudinal axis and has a proximal diameter, the distal portion is curved to space the distal end away from the longitudinal axis and has a distal diameter that is less than the proximal diameter, and the intermediate portion tapers in outer diameter going from the first end of the intermediate portion to the second end of the intermediate portion;

wherein the elongate body comprises an outer shaft that extends between the proximal end of the elongate body and the first end of the intermediate portion, and an inner shaft received in the outer shaft and defining the lumen, the inner shaft extending between the proximal end of the elongate body and the distal end of the elongate body.

2. The needle of claim 1, wherein:

the outer shaft has an outer shaft diameter that is constant; and the inner shaft has an inner shaft diameter that is constant.

3. The needle of claim 2, wherein the outer shaft diameter defines the proximal diameter and the inner shaft diameter defines the distal diameter.

4. The needle of claim 3, further comprising a filler received on the inner shaft in the intermediate portion, wherein the filler tapers in diameter going from the first end to the second end.

5. The needle of claim 4, wherein the filler has a first diameter at the first end of the intermediate portion and a second diameter at the second end of the intermediate portion, and wherein the first diameter is equal to the proximal diameter, and the second diameter is equal to the distal diameter.

6. The needle of claim 2, wherein:

the elongate body further comprises a sleeve in which the inner shaft and outer shaft are received;

the sleeve extends between the proximal end of the elongate body and the second end of the intermediate portion;

the sleeve has a first sleeve diameter that is constant between the proximal end of the elongate body and the first end of the intermediate portion; and the sleeve tapers in diameter between the first end and the second end of the intermediate portion.

7. The needle of claim 6, wherein the first sleeve diameter defines the proximal diameter.

8. The needle of claim 7, wherein the sleeve has a second diameter at the second end of the intermediate portion, and the second diameter is equal to the distal diameter.

9. The needle of claim 1, wherein:

the outer shaft extends between the proximal end of the elongate body and the second end of the intermediate portion;

the outer shaft has an outer shaft diameter that is constant between the proximal end of the elongate body and the first end of the intermediate portion, wherein the outer shaft diameter defines the proximal diameter; and the outer shaft tapers in diameter between the first end and the second end of the intermediate portion.

10. The needle of claim 9, wherein the outer shaft has a first diameter at the first end of the intermediate portion and a second diameter at the second end of the intermediate portion, wherein the first diameter is equal to the proximal diameter and the second diameter is equal to the distal diameter.

11. The needle of claim 1, wherein the hub comprises an indicator of a direction of the curve of the distal portion.

12. The needle of claim 1, wherein:

the elongate body comprises an inner surface defining the lumen and an outer surface spaced radially from the inner surface; and at the distal end of the elongate body, the inner surface is radiused.

13. A medical assembly comprising:

a needle including a hub, an elongate body, and a lumen, wherein the elongate body has a proximal portion joined to the hub and defining a proximal end of the elongate body, a distal portion opposite the proximal portion and defining a distal end of the elongate body, and an intermediate portion between the proximal portion and the distal portion and having a first end adjacent the proximal portion and a second end adjacent the distal portion, wherein the lumen extends longitudinally through the elongate body, and wherein the proximal portion extends linearly along a longitudinal axis and has a proximal diameter, the distal portion is curved to space the distal end away from the longitudinal axis and has a distal diameter that is less than the proximal diameter, and the intermediate portion tapers in diameter going from the first end to the second end, wherein the elongate body comprises an outer shaft that extends between the proximal end of the elongate body and the first end of the intermediate portion, and an inner shaft received in the outer shaft and defining the lumen, the inner shaft extending between the proximal end of the elongate body and the distal end of the elongate body; and a guidewire advanceable through the lumen from the proximal end to the distal end of the elongate body.

14. The medical assembly of claim 13, wherein the guidewire has a guidewire distal portion and a guidewire proximal portion;

the guidewire comprises a core wire and a coil received on the core wire in the distal portion; and the guidewire comprises a smooth transition between the core wire and the coil.

15. The medical assembly of claim 14, wherein to provide the smooth transition, the core wire comprises a ramp proximal of the coil.

16. The medical assembly of claim 14, wherein to provide the smooth transition, the core wire comprises a cut-out in which the coil is seated.

17. The medical assembly of claim 13, further comprising a catheter insert received in the lumen and having a shield, wherein the catheter insert is movable between a retracted configuration in which the shield is received in the lumen and a deployed configuration in which the shield is positioned proud of the distal end of the needle and shields the guidewire from the distal end of the needle during retracting of the guidewire.

18. The medical assembly of claim 17, wherein the shield has a blunt end surface and a proximally facing surface that defines a shoulder for engaging and covering the sharp distal end.

19. A medical assembly comprising:

a needle including a hub, an elongate body, and a lumen extending longitudinally through the elongate body, wherein the elongate body has a proximal portion joined to the hub and defining a proximal end of the elongate body, and a distal portion opposite the proximal portion and defining a sharp distal end of the elongate body;

a guidewire that is advanceable through the lumen to position a guidewire distal portion proud of the sharp distal end and that is retractable through the lumen to withdraw the guidewire distal portion back into the lumen; and a catheter insert received in the lumen and having a shield, wherein the catheter insert is movable between a retracted configuration in which the shield is received in the lumen and a deployed configuration in which the shield is positioned proud of the sharp distal end and shields the guidewire from the sharp distal end during retracting of the guidewire;

wherein the shield has a blunt end surface and a proximally facing surface that defines a shoulder for engaging and covering the sharp distal end.

20. The medical assembly of claim 19, wherein the catheter insert comprises a sleeve and wherein the shield comprises a tip of the sleeve.

\* \* \* \* \*